United States Patent
Cooney et al.

(10) Patent No.: US 7,153,965 B2
(45) Date of Patent: Dec. 26, 2006

(54) PHARMACEUTICALLY ACCEPTABLE INORGANIC AND ORGANIC SALTS OF 5-METHYLPYRAZINE-2-CARBOXYLIC ACID-4-OXIDE

(75) Inventors: Mark Cooney, Grove City, OH (US); Jonathan Caudill, Ashville, OH (US); Satish C. Nigam, Hilliard, OH (US)

(73) Assignee: ISP Investments Inc., Wilmington, DE (US)

( * ) Notice: Subject to any disclaimer, the term of this patent is extended or adjusted under 35 U.S.C. 154(b) by 290 days.

(21) Appl. No.: 10/848,098

(22) Filed: May 18, 2004

(65) Prior Publication Data

US 2005/0261312 A1    Nov. 24, 2005

(51) Int. Cl.
*C07D 241/02* (2006.01)
(52) U.S. Cl. .................................................... 544/406
(58) Field of Classification Search ............... None
See application file for complete search history.

(56) References Cited

U.S. PATENT DOCUMENTS

| | | | |
|---|---|---|---|
| 4,002,750 A | 1/1977 | Ambrogi et al. ............ 424/250 |
| 4,051,245 A | 9/1977 | Ambrogi et al. ............ 424/250 |
| 4,866,178 A | 9/1989 | Venturello et al. ......... 544/406 |

FOREIGN PATENT DOCUMENTS

| | | |
|---|---|---|
| EP | 0201934 | 11/1986 |
| JP | 62-263164 | 11/1987 |
| JP | 1224365 | 9/1989 |

OTHER PUBLICATIONS

McKay et al, "Oxidation Methods for Aromatic Diazines: Substituted Pyrazine N-Oxides, Pyrazine N,N'-Dioxides, and 2,2':6:,2"-Terpyridine-1,1"-Dioxide" Heterocyclic Communications, vol. 7(4), pp. 307-312 (2001).*

* cited by examiner

*Primary Examiner*—Zachary C. Tucker
(74) *Attorney, Agent, or Firm*—William J. Davis; Imre Balogh

(57) ABSTRACT

Methods for the preparation of pharmaceutically acceptable organic or inorganic salts of 5-methylpyrazinecarboxylic acid-4-oxide esters including tris(hydroxymethyl)aminomethanol, N,N-dimethylethanolamine, N-methyl-D-glucamine, L-Lysine, L-arginine, Na, K, Ca and Mg. The esters of 5-methylpyrazinecarboxylic acid-4-oxide are oxidized in aqueous hydrogen peroxide at a pH of 2.5 to 7 in the presence of a catalyst selected from the group consisting of sodium tungstate, tungstic acid and ammonium heptamolybdate. The salts are formed by saponification of the esters followed by alcohol precipitation, or by reaction with a metal trimethylsilanoate, or by the reaction of organic bases with the saponified acids.

10 Claims, No Drawings

PHARMACEUTICALLY ACCEPTABLE INORGANIC AND ORGANIC SALTS OF 5-METHYLPYRAZINE-2-CARBOXYLIC ACID-4-OXIDE

BACKGROUND OF THE INVENTION

1. Field of the Invention

This invention relates to a process for the preparation of esters of 5-methylpyrazine-2-carboxylic acid-4-oxide and its conversion to pharmaceutically acceptable organic and inorganic salts thereof.

2. Description of the Related Art

It has been our endeavor to synthesize the pharmacological acceptable salts of the 5-methylpyrazinecarboxylic acid via a novel route that will allow us to manufacture these in high purity.

Hydrogen peroxide combined with tungstic acid is an inexpensive, versatile and relatively stable oxidizing agent that has been widely used for a number of functional group transformations including epoxidation of alkenes, diol formation, oxidative alkene cleavage to form dioic acids, and formation of α-hydroxy ketones. Tungstic acid and hydrogen peroxide are also known to oxidize sulfides to sulfones, and amines to oximes, nitrones, hydroxamic acids, and nitroso compounds.

Sodium tungstate has been used in combination with hydrogen peroxide for the conversion of the 5-methylpyrazinecarboxamide-4-oxide. Hydrogen peroxide in combination with ammonium heptamolybdate is known for epoxide formation and the oxidation of secondary alcohols in preference to primary alcohols.

5-Methylpyrazinecarboxylic acid-4-oxide has been produced by several methods described in the literature. Examplary methods include the following.

1. It is made by the oxidation of the 5-methylpyrazinecarboxylic acid using hydrogen peroxide and a tungstate or molybdate catalysts as described in Japanese Patents No. 62263164 and European Patent No. 201934.
2. It is also prepared by peracid oxidation of the 5-methylpyrazinecarboxamide (from a mixed anhydride) followed by basic hydrolysis of the amide oxide and pH adjustment (U.S. Pat. No. 4,051,245).

We have chosen a more stable intermediate, the corresponding esters in place of the acid and the carboxamide, to bring about this transformation. This allows us to produce the material in very high purity as the pure intermediates can either be used as such or can be further purified.

SUMMARY OF THE INVENTION

In accordance with the present invention, ester ($C_{1-4}$) and organic and inorganic salts of 5-methylpyrazinecarboxylic acid are prepared as shown hereunder

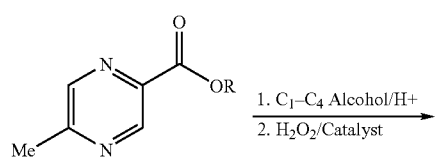

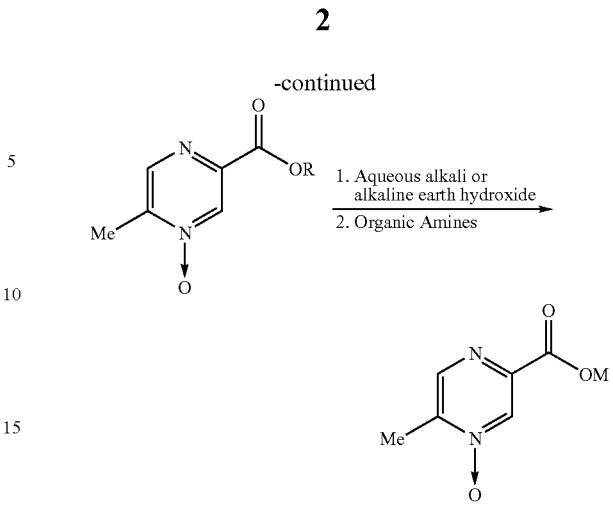

wherein:

R is a hydrogen atom or an alkyl group having from 1 to 4 carbon atoms; and

M is an inorganic salt of Na, K, Mg and Ca; or an organic salts of tris (hydroxymethyl)aminomethanol, N,N-dimethylethanolamine, N-methyl-D-glucamine, L-lysine, and L-arginine.

Esters ($C_{1-4}$) of 5-methylpyrazinecarboxylic acid are prepared by heating the acid with the appropriate $C_{1-4}$ alcohol in the presence of mineral acids such as sulfuric, hydrochloric, or AMBERLYST® 15 ion which is a trademark name for an acidic cation exchange resin (20–40 wt %). The ester is oxidized in a homogeneous system consisting of a either a tungstate or molybdate catalyst and 35% hydrogen peroxide at a pH ranging between 2.5 and 7. Saponification of the oxidation product with an appropriate aqueous alkali or alkaline earth hydroxide results in formation of the desired salt. Alternatively, sodium or potassium salts are prepared by addition of sodium or potassium trimethylsilanolate to a homogeneous solution of the oxidized ester in ether solvents such as diethyl ether or THF.

DETAILED DESCRIPTION OF THE INVENTION

It is known that the 5-methylpyrazinecarboxylic acid-4-oxide exhibits hypoglycaemic and hypolipaemic activity. This product is used as such but can result in severe irritation of the gastrointestinal lining because of its low pH. The present invention relates to a scalable process for the manufacture of different esters of the 5-methylpyrazinecarboxylic acid-4-oxide that exhibit slightly diminished hypoglycaemic and hypolipaemic activity. These products are used as such but can also be saponified yielding different (Na, K, Mg, and Ca) salts or by the reaction of organic bases with acids of the saponified esters that should have similar pharmacological activity to the corresponding acid but should be better tolerated.

This invention also relates to a novel way of accomplishing the transformation (via esters) to these pharmaceutically acceptable salts. Preparation of the N-oxide uses safe, inexpensive, and easily handled catalysts that allow the reaction to be carried out in a slight excess of hydrogen peroxide at moderate temperatures and in good yield.

In accordance with the present invention and unlike other methods described in prior art, the reaction is carried out in a homogeneous system that consists of 35% hydrogen peroxide in combination with a catalytic amount of sodium tungstate, tungstic acid (prepared in situ from sodium tungstate and sulfuric acid) or acidified ammonium heptamolybdate. The catalyst is generally used in amount ranging from 2.5 to 9 mol % (based on 5-methylpyrazinecarboxylic acid ester). Generally, 2.5 to 3 mol % of catalyst is preferred. The catalyst is dissolved in water and aqueous 50% sulfuric acid is added until the pH is between 3 and 4 (alternatively the reactions can be run without adding sulfuric acid, however, at a pH much above 4 there is the increased possibility of 1-oxide formation). The solution is stirred for 15 to 30 minutes followed by addition of 1.3 to 2.5 equivalents, preferably 1.3 to 1.45 equivalents of 35% aqueous hydrogen peroxide. The solution is then stirred for 15 to 30 minutes to allow complete reaction of the hydrogen peroxide with the catalyst. The substrate is added, and the reaction mixture is stirred at 65° C. to 75° C., preferably at 70° C. Typical reaction times are 6 to 28 hours (usually about 12 h, monitor by GC or GC/MS). The solvent is removed under reduced pressure at a temperature ≦60° C. The reaction mixture is then cooled in an ice bath and the solid product is collected by filtration, washed with ice-cold water. The isolated ester oxide is dried under vacuum at about 60° C.

The ester oxides can then be saponified, typically with sodium hydroxide, at 50° C. and a pH range of 8 to 13 with a pH of 9 to 9.5 being preferable. The product is precipitated by the addition of a pharmaceutically acceptable alcohol such as ethanol, isopropanol, or an appropriate specifically denatured alcohol (SDA). Alternatively, the ester N-oxide may be taken up in diethyl, THF, dichloromethane or toluene, with THF being preferable. The solution (filter if necessary) is then stirred with sodium or potassium trimethylsilanolate at 0° C. to 25° C., preferably at 10° C. to 15° C., for 4 hours. The precipitated sodium or potassium salt is collected by filtration and dried to constant weight under vacuum at 50° C. to 65° C. The following further illustrates the process that is described in detail in conjunction with the non-limiting examples.

EXAMPLE 1

The reaction was carried out, under nitrogen, in a 1 L×4 neck flask equipped with a mechanical stirrer, water condenser (with gas inlet), and a thermocouple. The reactor was charged with 5-methylpyrazinecarboxylic acid (100 g), and acidic cation exchange resin (20 g), and methanol (300 g). The mixture was stirred at reflux for about 20 h. After the reaction was complete (analyze with GC or GC/MS), the resin was removed by pressure filtration. The resin was rinsed with methanol and about 75% of the solvent was removed under reduced pressure. The resulting suspension was allowed to stand at room temperature overnight, and then in an ice-bath for 3 h. The solid was collected by filtration and washed with ice-cold methanol (2×80 g). Drying under vacuum at room temperature (25 inches of Hg) yielded 102.4 g (93%) of 5-methyl-2-pyrazinecarboxylic acid, methyl ester that was suitable for further use.

EXAMPLE 2

The reaction is carried out, under nitrogen, in a 1 L×4 neck flask equipped with a mechanical stirrer, water condenser (with gas inlet), and a thermocouple. The reactor is charged with 5-methylpyrazinecarboxylic acid (100 g), ethanol (300 g) and sulfuric acid (2 g). The contents are refluxed for eight hours at 78° C. The reaction mixture is cooled to ambient temperature and sodium bicarbonate (4 g) is added. About 75% of the solvent is removed under reduced pressure and the resulting suspension is allowed to stand overnight. The solids are filtered and washed with cold methanol (2×80 g). Drying under oven (25 inches of Hg) yielded 101.25 g (84%) of 5-methyl-2-pyrazinecarboxylic acid, ethyl ester.

EXAMPLE 3

The reaction was carried out, under nitrogen, in a 2 L×4 neck flask equipped with a mechanical stirrer, water condenser (with gas inlet), and a thermocouple. The reactor was charged with 5-methylpyrazinecarboxylic acid (300.84 g), an acidic cation exchange resin (60.17 g), and ethanol (1004 g). The mixture was stirred at reflux for about 16 h after which the reaction was found to be complete by GC or GC/MS. The resin was removed by pressure filtration and rinsed with ethanol. The rinse was added to the alcohol solution of the ester. Evaporation of the solvent under reduced pressure gave 336.7 g (93%) of 5-methylpyrazinecarboxylic acid, ethyl ester that was suitable for use in the following examples. It was also possible to pass the material through a thin film evaporator at 125° C./3 mm. The material from this distillation was almost colorless and crystallizes at about 20° C.

EXAMPLE 4

The reaction was carried out, under nitrogen, in a 500 mL×4 neck flask equipped with a mechanical stirrer, water condenser (with gas inlet), and a thermocouple. The reactor was charged with sodium tungstate dihydrate (1.35 g) and water (30 g). The mixture was stirred to dissolve the solid (10 minutes). Aqueous sulfuric acid (50%) was added bringing the pH down to about 3.5. Aqueous 35% hydrogen peroxide (22.36 g) was added and the solution was stirred for 15 minutes. 5-Methylpyrazinecarboxylic acid ethyl ester (27.27 g) was then added. The reaction mixture was warmed to 70° C. and then stirred for a total of 12 hours after which the reaction was checked by GC or GC/MS and was found to be complete. The resulting solution was concentrated under reduced pressure to yield a light yellow solid. The reaction mixture was cooled in an ice-bath for 3 hours. The product was collected by filtration and washed with ice water (25 g). Drying the solid at 60° C. under house vacuum yielded 20.57 g (69%) of the ester N-oxide.

EXAMPLE 5

The reaction was carried out, under nitrogen, in a 500 mL×4 neck flask equipped with a mechanical stirrer, water condenser (with gas inlet), and a thermocouple. The reactor was charged with 5-methylpyrazinecarboxylic acid-4-oxide, ethyl ester (8.12 g), and water (23 g). A solution of sodium hydroxide (1.96 g) in water (6 g) was added over 20 minutes at ≦6° C., and then the reaction mixture was warmed to 50° C. and stirred for 30 minutes. The reaction mixture was cooled to room temperature and then concentrated HCl (0.41 g) was added bringing the pH to below 9. Isopropyl alcohol (40 g) was added to the reaction mixture over about 1 hour at room temperature to precipitate the salt followed by overnight stirring. After stirring the suspension in an ice-bath for 3.5 h, the solid was collected and rinsed with ice-cold isopropyl alcohol (3×15 g). The collected solid is dried under vacuum (25 inches of Hg at 60° C.) to yield 5.63 g (72%) of the sodium salt as a off-white solid.

EXAMPLE 6

The reaction was carried out, under nitrogen, in a 500 mL×4 neck flask equipped with a mechanical stirrer, water condenser (with gas inlet), and a thermoccouple. The reactor was charged with sodium trimethylsilanolate (3.71 g) and THF (90 g). 5-Methylpyrazinecarboxylic acid-4-oxide, ethyl ester (6.00 g) was added and the mixture was stirred for 4 h at room temperature. The solid was collected and rinsed with THF (3×45 g). Drying under vacuum (25 inches of Hg at 65° C.) yielded 5.59 g (96%) of the sodium salt as an off-white solid.

EXAMPLE 7

The reaction was carried out, under nitrogen, in a 500 mL×4 neck flask equipped with a mechanical stirrer, water condenser (with gas inlet), and a thermocouple. The reactor was charged with 5-methylpyrazinecarboxylic acid-4-oxide, ethyl ester (8.12 g) and methanol (23 g). A solution of sodium hydroxide (1.96 g) in water (6 g) was added over 20 minutes at ≦6° C., and then the reaction mixture was warmed at 50° C. and stirred for 30 minutes. The reaction mixture was cooled to room temperature and concentrated HCl (0.41 g) was added bringing the pH to below 7. Methanol (40 g) was added to the reaction mixture with stirring. N-methyl-D-glucamine was added and the mixture refluxed for one hour. After stirring the suspension in an ice-bath for 3.5 h, the solid was collected and rinsed with ice-cold methanol (3×15 g). The collected solid is dried under vacuum (25 inches of Hg at 60° C.) to yield 80% of the glucamine salt as a off-white solid.

It will be understood that changes and modification may be made to the present invention which are within the skill of the art. Such changes and modifications are intended to be covered limited only by the scope of the appended claims.

What is claimed is:

1. A method for the preparation of 5-methylpyrazinecarboxylic acid-4-oxide esters comprising:
    reacting 5-methylpyrazinecarboxylic acid with a $C_{1-4}$ alcohol in the presence of an acidic cation exchange resin, and
    oxidizing the so-obtained ester in a homogeneous system consisting of a tungstate or molybdate catalyst and 35% w/w hydrogen peroxide at a pH range of 2.5 to 7.

2. A method for the preparation of the pharmaceutically acceptable organic and inorganic salts of 5-methylpyrazinecarboxylic-4-oxide comprising:
    oxidizing an ester of 5-methylpyrazinecarboxylic acid in a homogeneous system consisting of either a tungstate or molybdate catalyst and about 35% w/w hydrogen peroxide at a pH of from about 2.5 to about 7; and
    saponifying said oxidized ester with an aqueous alkali or alkaline earth hydroxide to obtain the salt of 5-methylpyrazinecarboxylic-4-oxide.

3. A method for the preparation of a pharmaceutically acceptable inorganic or organic salt of a 5-methylpyrazinecarboxylic acid-4-oxide having the formula I

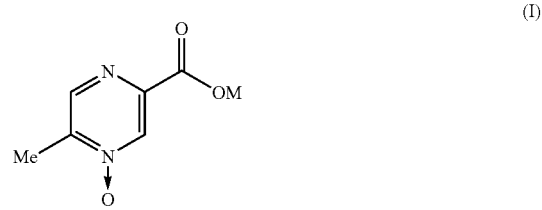

(I)

wherein
    M is selected from the group of alkali metal and alkaline earth metal cations consisting of Na, K, Mg, Ca, and the conjugate acid of amine bases selected from the group consisting of tris(hydroxymethyl) aminomethanol, N,N-dimethylanolamine, N-methyl-D-glucamine, L-lysine and L-arginine, comprising the steps of:
    reacting 5-methylpyrazinecarboxylic acid-4-oxide having the formula II

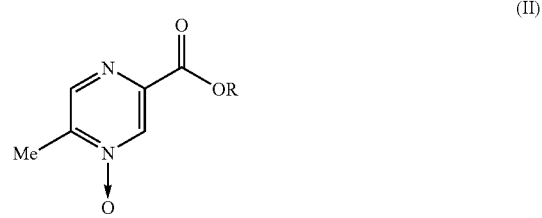

(II)

wherein
    R is H with a $C_{1-4}$alcohol in the presence of 20–40% w/w acidic cation exchange resin to obtain an ester of the formula III

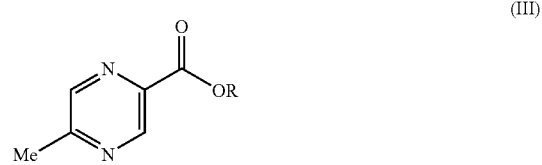

(III)

wherein
    R is $C_{1-4}$ alkyl;
    oxidizing the ester of formula III in a homogeneous system consisting of either a tungstate or molybdate catalyst and about 35% hydrogen peroxide at a pH of from about 2.5 to about 7; and saponifying the oxidation product with an aqueous alkali or alkaline earth hydroxide or with an organic salt forming agent to obtain the salt of formula I.

4. A method for the preparation of a pharmaceutically acceptable organic or inorganic salt of 5-methylpyrazinecarboxylic acid-4-oxide having the formula I

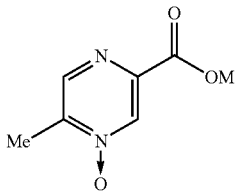

wherein
  M is selected from the group consisting of alkali metal and alkaline earth metal cations consisting of Na, K, Mg, Ca and the conjugate acid of the amine bases selected from the group consisting of tris(hydroxymethyl)/aminomethanol, N, N-dimethylethanolamine, N-methyl-D-glucamine, L-lysine, and L-arginine, comprising the steps of:
    preparing a homogeneous system consisting of about 35% w/w/hydrogen peroxide and a 2.5 to 9 mole % of a catalyst selected from the group consisting of sodium tungstate, tungstic acid and acidified ammonium heptamolybdate;
    dissolving said catalyst in water,
    adding 50% w/w sulfuric acid until reaching a pH of 3 to 4 to obtain a solution;
    adding about 1.3 to 2.5 equivalents of 35% w/w of aqueous hydrogen peroxide to allow said catalyst to completely react with said aqueous hydrogen peroxide;
    adding one molar equivalent of 5-methylpyrazinecarboxylic acid ester and stirring the system at 65° C. to 75° C. for 6 to 28 hrs to obtain a reaction mixture;
    cooling the reaction mixture;
    collecting the solid product by filtration;
    washing the collected product with ice-cold water;
    drying the washed isolated ester oxide under vacuum at about 60° C.;
    saponifying the ester oxide with an aqueous alkali hydroxide or with an organic salt forming agent at about 50° C. and a pH range of 8 to 15; and
    precipitating the salt of 5-methylpyrazinecarboxylic acid oxide by a pharmaceutically acceptable alcohol selected from the group consisting of ethanol, isopropanol and specially denatured alcohol to obtain the product of formula I.

5. The method of claim 4 wherein said tungstic acid is prepared in situ from sodium tungstate and sulfuric acid.

6. The method of claim 4 wherein said saponifying is with sodium, potassium, calcium or magnesium hydroxide.

7. A method for the preparation of a pharmaceutically acceptable inorganic salt of 5-methylpyrazinecarboxylic acid-4-oxide having the formula I

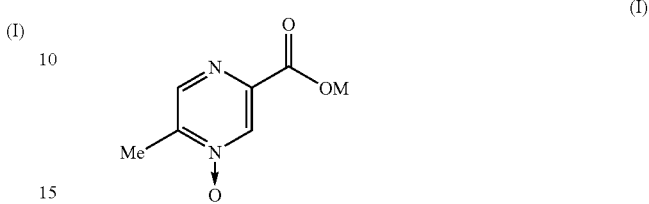

wherein
  M is selected from the group consisting of alkali metal and alkaline earth metal cations consisting of Na, K, Mg, and Ca, comprising the steps of:
    preparing a homogeneous system consisting of about 35% w/w/hydrogen peroxide and a 2.5 to 9 mole % of a catalyst selected from the group consisting of sodium tungstate, tungstic acid and acidified ammonium heptamolybdate;
    dissolving said catalyst in water;
    adding 50% w/w sulfuric acid until reaching a pH of 3 to 4 to obtain a solution;
    adding about 1.3 to 2.5 equivalents of 35% w/w of aqueous hydrogen peroxide to allow said catalyst to completely react with said aqueous hydrogen peroxide;
    adding one molar equivalent of 5-methylpyrazinecarboxylic acid and stirring the system at 65° C. to 75° C. for 6 to 28 hrs to obtain a reaction mixture;
    cooling the reaction mixture;
    collecting the solid product by filtration;
    washing the collected product with ice-cold water;
    drying the washed isolated ester oxide under vacuum at about 60° C.;
    saponifying the ester oxide in diethyl ether, 2,3,4,5-tetrahydrofuran or toluene to obtain a solution;
    collecting the resulting inorganic salt by filtration; and
    drying the salt at 50° C. to 65° C. under vacuum.

8. The method of claim 7 wherein said catalyst is present in amounts of 2.5 to 3 mol %.

9. The method of claim 7 wherein said 35% hydrogen peroxide is present in about 1.3 to 1.45 equivalents.

10. The method of claim 7 wherein said saponification is at a pH of about 9 to 9.5.

* * * * *